US00RE46697E

(19) United States
(12) Reissued Patent
Hayes, Jr.

(10) Patent Number: US RE46,697 E
(45) Date of Reissued Patent: Feb. 6, 2018

(54) USE OF ENDOVASCULAR HYPOTHERMIA IN ORGAN AND/OR TISSUE TRANSPLANTATIONS

(75) Inventor: Kenneth G. Hayes, Jr., Menlo Park, CA (US)

(73) Assignee: ZOLL Circulation, Inc., San Jose, CA (US)

(21) Appl. No.: 11/725,845

(22) Filed: Dec. 8, 2009

(65) Prior Publication Data

US 2007/0213793 A1 Sep. 13, 2007

Related U.S. Patent Documents

Reissue of:
(64) Patent No.: 6,692,519
Issued: Feb. 17, 2004
Appl. No.: 09/923,683
Filed: Aug. 6, 2001

U.S. Applications:
(62) Division of application No. 11/351,216, filed on Feb. 8, 2006, which is an application for the reissue of Pat. No. 6,692,519.

(51) Int. Cl.
*A61F 7/00* (2006.01)
*A61F 7/12* (2006.01)

(52) U.S. Cl.
CPC ..... *A61F 7/12* (2013.01); *A61F 7/123* (2013.01); *A61F 2007/0001* (2013.01); *A61F 2007/0056* (2013.01); *A61F 2007/0063* (2013.01); *A61F 2007/126* (2013.01)

(58) Field of Classification Search
CPC ..... A61F 2007/0001; A61F 2007/0056; A61F 2007/0063; A61F 2007/126; A61F 7/12; A61F 7/123
USPC ..... 128/898; 604/113; 606/20–26; 607/104, 607/105
See application file for complete search history.

(56) References Cited

U.S. PATENT DOCUMENTS

| | | | | |
|---|---|---|---|---|
| 4,723,939 | A * | 2/1988 | Anaise | 604/113 |
| 5,149,321 | A | 9/1992 | Klatz et al. | |
| 5,234,405 | A | 8/1993 | Klatz et al. | |
| 5,395,314 | A | 3/1995 | Klatz et al. | |
| 5,486,208 | A | 1/1996 | Ginsburg | |
| 5,574,019 | A * | 11/1996 | Segall et al. | 514/23 |
| 5,584,804 | A | 12/1996 | Klatz et al. | |

(Continued)

FOREIGN PATENT DOCUMENTS

| | | |
|---|---|---|
| WO | WO 95/11055 | 4/1995 |
| WO | WO 00/010494 | 3/2000 |
| WO | WO 01/043661 | 6/2001 |

*Primary Examiner* — Cary Wehner
(74) *Attorney, Agent, or Firm* — Robert D. Buyan; Stout, Uxa & Buyan, LLP

(57) ABSTRACT

Methods for (a) preventing hypoxic damage to a potentially transplantable organ or tissue prior to explanation of that organ or tissue from the body of a mammalian transplant donor and (b) preventing rejection of a transplanted organ or tissue in a human or veterinary transplant recipient. The methods comprise placing a heat exchange apparatus in the vasculature of the donor or recipient and using that heat exchange apparatus to cool at least a portion of the body of the donor or recipient to a temperature below normothermia (e.g. below normothermia and sometimes between about 30° C. and about 36° C.).

26 Claims, 11 Drawing Sheets

(56) References Cited

U.S. PATENT DOCUMENTS

| | | | | |
|---|---|---|---|---|
| 5,701,746 | A * | 12/1997 | Desgrandchamps et al. | 62/62 |
| 5,709,654 | A | 1/1998 | Klatz et al. | |
| 5,752,929 | A | 5/1998 | Klatz et al. | |
| 5,827,222 | A | 10/1998 | Klatz et al. | |
| 5,837,003 | A | 11/1998 | Ginsburg | |
| 5,957,963 | A | 9/1999 | Dobak, III | |
| 6,030,412 | A | 2/2000 | Klatz et al. | |
| 6,080,538 | A * | 6/2000 | Segall et al. | 435/1.2 |
| 6,096,068 | A | 8/2000 | Dobak, III et al. | |
| 6,110,168 | A | 8/2000 | Ginsburg | |
| 6,126,684 | A | 10/2000 | Gobin et al. | |
| 6,146,411 | A | 11/2000 | Noda et al. | |
| 6,149,670 | A | 11/2000 | Worthen et al. | |
| 6,149,673 | A | 11/2000 | Ginsburg | |
| 6,149,676 | A | 11/2000 | Ginsburg | |
| 6,224,624 | B1 * | 5/2001 | Lasheras et al. | 607/105 |
| 6,231,594 | B1 | 5/2001 | Dae | |
| 6,264,679 | B1 | 7/2001 | Keller et al. | |
| 6,410,218 | B2 * | 6/2002 | Segall et al. | 435/1.2 |
| 6,413,233 | B1 * | 7/2002 | Sites et al. | 604/6.13 |
| 6,444,418 | B2 * | 9/2002 | Segall et al. | 435/1.2 |
| 6,497,721 | B2 | 12/2002 | Ginsburg et al. | |
| 6,620,188 | B1 | 9/2003 | Ginsburg et al. | |
| 6,736,836 | B2 * | 5/2004 | Montgomery | 607/104 |

* cited by examiner

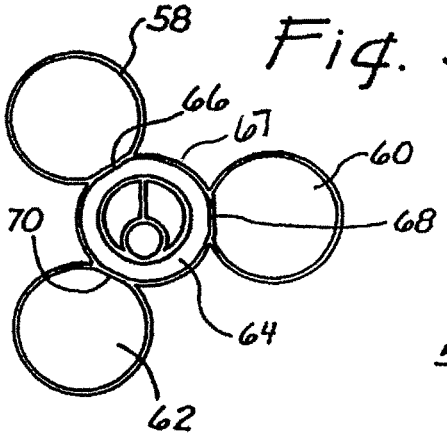
Fig. 3
(Amended)
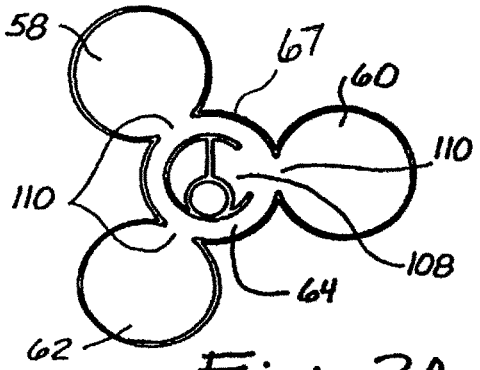
Fig. 3A
(Amended)
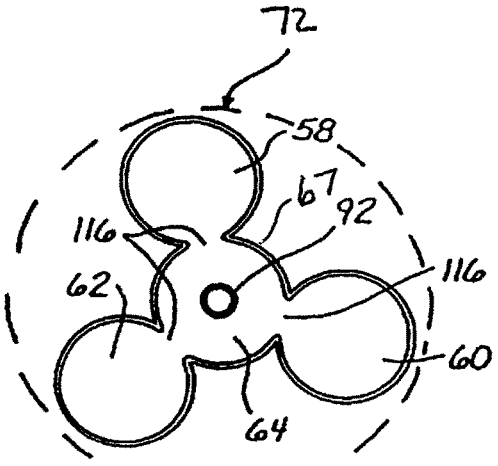
Fig. 5
(Amended)
Fig. 4
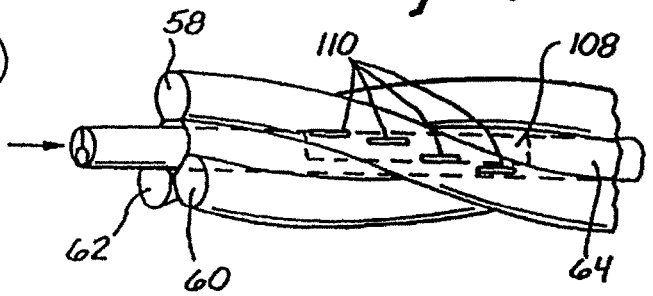

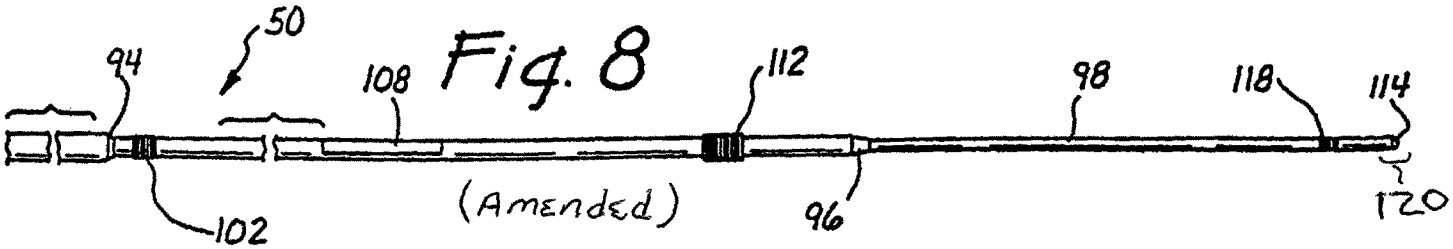
Fig. 8 (Amended)

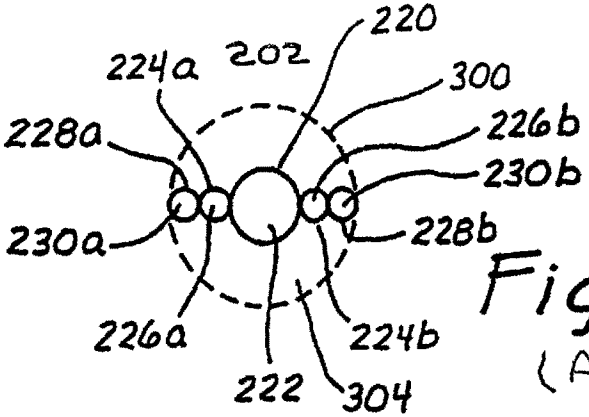
Fig. 11A
(Amended)

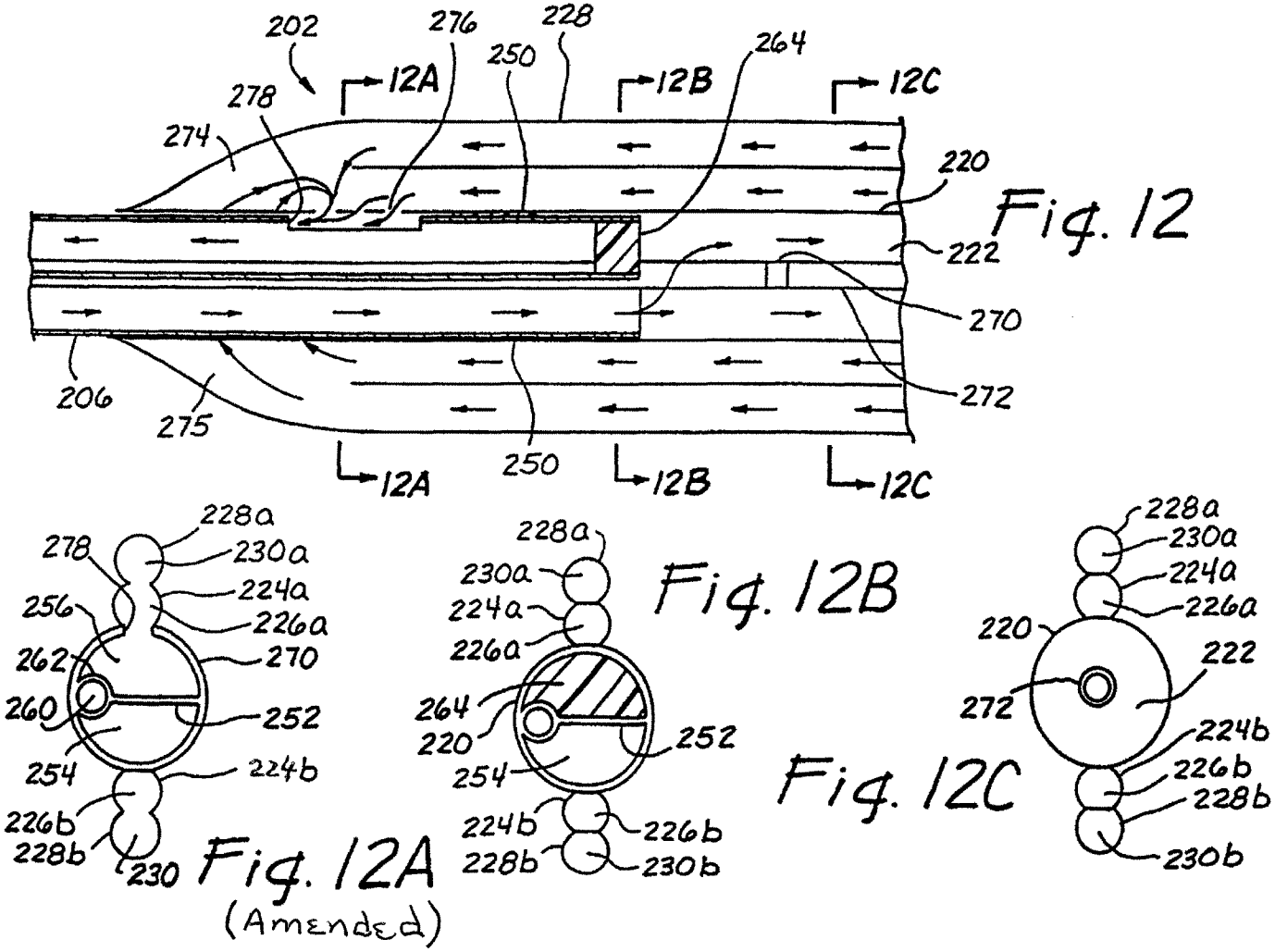
Fig. 12
Fig. 12B
Fig. 12C
Fig. 12A (Amended)

USE OF ENDOVASCULAR HYPOTHERMIA IN ORGAN AND/OR TISSUE TRANSPLANTATIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*RELATED APPLICATIONS*

*This is a division of U.S. Reissue application Ser. No. 11/351,216 filed Feb. 8, 2006, which is based on U.S. Pat. No. 6,692,519, which issued Feb. 17, 2004 from application Ser. No. 09/923,683 filed Aug. 6, 2001.*

FIELD OF THE INVENTION

This invention relates generally to methods for human or veterinary medical treatment and more particularly to a) the endovascular application of hypothermia to beating heart donors prior to harvesting of organ(s) and/or tissue(s) for transplantation to avoid hypoxic damage to the organ(s) and/or tissue(s) and b) the endovascular (e.g., intravascular) application of hypothermia to transplant recipients during and/or after transplantation of organ(s) and/or tissue(s) to reduce acute inflammatory response and help avoid acute transplant rejection and/or other complications.

BACKGROUND OF THE INVENTION

In the early days of organ transplantation, all cadaveric (non-living) organ donors were pronounced dead by loss of heart function or "cardiac death" criteria. However, in the late 1960's and early 1970's "brain death" criteria were developed that allowed organs to be harvested from donors who's hearts were still beating but who had been pronounced dead based on the irreversible cessation of all brain activity. Additionally, it was learned that organ transplantation was more successful in cases where the donor's respiration and circulation were supported by artificial means (e.g., the use of mechanical ventilation and the administration of pharmacologic or mechanical support of cardiac activity) after brain death had occurred until the organs could be removed for transplantation. This "beating heart donor" technique enables oxygenated blood to continue to flow through the organs until immediately before they are harvested from the donor, thereby enhancing the organs' viability.

Every day, approximately ten people die in the United States while awaiting an organ transplant, simply because suitable donor organs are not available for them in time. Various approaches have been proposed for making transplantable organs more readily available to patients in need of transplants. For example, research is underway to develop genetically or immunologically modified animals who's organs may be suitable for xenotransplantation (i.e., transplantation of an organ or tissue from one species of animal into another species of animal) in humans. However, it remains uncertain as to whether xenotransplantation research will ultimately give rise to universally useable organs of all needed types and even if the current research is successful, the potential clinical implementation of xenotransplantation techniques remains many years away.

Another approach has been to obtain some types of organs from human cadaveric donors who have been declared dead by traditional cardiac death criteria as opposed to brain death criteria. However, a number of important transplantable organs (e.g., hearts) can not typically be harvested from cadaveric donors more than just a few minutes after the cardiac death has occurred because the viability of the organ is lost.

On Jan. 6,2001 The United Network for Organ Sharing (UNOS) national patient waiting list for organ transplant included the following:

| Type of Transplant | Patients Waiting for Transplant |
|---|---|
| kidney transplant | 47,689 |
| liver transplant | 16,815 |
| pancreas transplant | 1,033 |
| pancreas islet cell transplant | 178 |
| kidney-pancreas transplant | 2,457 |
| intestine transplant | 147 |
| heart transplant | 4,152 |
| heart-lung transplant | 206 |
| lung transplant | 3,676 |
| *Total Patients Total | *73,989 |

However, because of the shortage of suitable donor organs, the number of organ transplants that will actually be performed during the year 2001 is likely to be substantially lower than the number of patients on the waiting list. During the year 2000, the number of transplants actually performed in the United States were as follows:

| Type of Transplant | Number |
|---|---|
| kidney alone transplants (5,227 were living donors) | 13,290 |
| liver transplants | 4,934 |
| pancreas alone transplants | 436 |
| kidney-pancreas transplants | 914 |
| intestine transplants | 79 |
| heart transplants | 2,197 |
| heart-lung transplants | 48 |
| lung transplants | 956 |
| Total | 22,854 |

Apart from the fact that the pool of potential organ donors is relatively small compared to the demand for transplantable organs, the shortage of organs is further exacerbated by the fact that sometimes, even after a potential donors family has agreed to organ donation, that donor's organs are lost because the donors cardiac activity can not be maintained for sufficient time to allow the necessary testing to establish and certify brain-death and to arrange for the arrival of the team of surgeons who are trained to remove the desired organ(s) from the donor's body. In view of these facts, there remains a need in the art for the development of new techniques to facilitate the harvesting of viable organs for transplantation so that more organs may be made available.

SUMMARY OF THE INVENTION

The present invention provides methods for decreasing the potential for hypoxic damage to transplantable organs in brain dead "beating heart" organ donors. The present invention also provides methods for preventing or treating episodes of acute transplant rejection in patients who have received organ or tissue transplants.

In accordance with one embodiment of the present invention, a heat exchange apparatus is inserted into the vasculature of a potential organ donor who is believed to be brain dead, but who has not yet been declared brain dead. The heat exchange apparatus is then used to cool the blood flowing through the potential donor's vasculature, thus cooling all of a portion of the donor's body to a desired temperature below normothermia (e.g., from about 37° C. to about 35° C. or less, often as low as 30°), thereby decreasing the oxygen demand of the tissues or organs to be transplanted and thus decreasing the likelihood that such tissues or organs will suffer hypoxic damage as a result of a hypoxic event while the patient is undergoing the necessary evaluation of his/her suitability as an organ donor, during the performance of testing necessary to confirm brain death (i.e., the "brain death work-up") and until such time as brain death has been certified and any organs deemed suitable for transplantation have been harvested from the donor's body. The types of hypoxic events that may occur during this period of time include periods of cardiac arrest where the donor's heart ceases to beat for a period of time, periods of extreme hypotension or periods where the mechanical ventilation is inadvertently or purposely interrupted.

Further in accordance with the present invention, a heat exchange apparatus is may be inserted into the vasculature of a potential organ donor who has already been declared brain dead but from whose body the organs or tissues desired for transplantation have not yet been harvested. The heat exchange apparatus is then used to cool the blood flowing through the potential donor's vasculature, thus cooling all of a portion of the donor's body to a desired temperature below normothermia (e.g., from about 37° C. to about 35° C. or less), thereby decreasing the oxygen demand of the tissues or organs to be transplanted and thus decreasing the likelihood that such tissues or organs will suffer hypoxic damage as a result of a hypoxic event while the patient is undergoing the necessary evaluation of his/her suitability as an organ donor and until such time as brain death has been certified and any organs deemed suitable for transplantation have been harvested from the donor's body. The types of hypoxic events that may occur during this period of time include periods of cardiac arrest where the donor's heart ceases to beat for a period of time, periods of extreme hypotension or periods where the mechanical ventilation is inadvertently or purposely interrupted.

Still further in accordance with the present invention, the heat exchange apparatus may be a pliable or flexible structure that is formed or mounted and configured to expand when filled with thermal exchange fluid. One or more lumens may extend through the catheter to permit infusion or circulation of thermal exchange fluid through the heat exchange apparatus in situ. The catheter may be initially inserted into the vasculature of the donor or recipient patient using well known percutaneous catheter insertion techniques and the catheter may then be advanced through the vasculature to a position where the heat exchange apparatus is situated at a desired location. The heat exchange apparatus may comprise a balloon or inflatable structure that is attached to one or more lumens of the catheter such that cooled thermal exchange fluid may be infused into or circulated through the heat exchange apparatus in situ. Blood flowing in heat exchanging proximity to the heat exchange apparatus will thereby become cooled. The subsequent circulation of the cooled blood will then cool all or a selected portion of the donor's or patient's body to the desired temperature below normothermia. The core body temperature or the temperature of a particular body part or organ of the donor or patient may be monitored and the temperature of the heat exchange apparatus may be modified periodically or continuously in response to the monitored temperature to prevent significant overshoot beyond the desired temperature and to thereafter maintain the temperature of the body or portion thereof at the desired temperature or within a range of desired temperatures, such as about 33° C. to about 30° C. An automated controller may be connected to temperature sensor(s) used to monitor the core body temperature or the temperature of the desired organ or portion of the donor's or patient's body. Also, such controller may be operatively connected to an apparatus that changes the temperature of the thermal exchange fluid being circulated through the heat exchange apparatus and/or the rate at which such thermal exchange fluid is circulated through the heat exchange apparatus. Based on the signal(s) received from the temperature sensor(s), the controller will then modify the temperature and/or rate of the thermal exchange fluid to optimize the cooling and maintenance of the temperature of the donor's or patient's body or portion thereof.

Further aspects and advantages of the present invention will become apparent to those of skill in the art upon reading and understanding the detailed descriptions of certain embodiments of the invention set forth herebelow and in the accompanying drawings.

BRIEF DESCRIPTION OF THE DRAWINGS

FIG. 3 is a cross-sectional drawing of the heat exchange region of the catheter taken along the line 3—3 in FIG. 1.

FIG. 3A is a cross-sectional view through line 3A—3A of FIG. 1.

FIG. 4 is a perspective drawing of a segment of the heat exchange region of the catheter within the circle 44 in FIG. 1.

FIG. 5 is a cross-sectional drawing of the heat exchange region of the catheter taken along the line 5—5 in FIG. 1

FIG. 8 is a perspective drawing of the distal portion of the shaft of one embodiment of the invention.

FIG. 11A is a cross sectional view of the heat exchange region taken along the line 11A—11A in FIG. 11.

FIG. 12 is a sectional view of the proximal portion of the heat exchange region of one embodiment of the invention.

FIG. 12A is a cross-sectional view of a portion of the heat exchange region taken along the line 12A—12A of FIG. 12.

FIG. 12B is a cross-sectional view of a portion of the heat exchange region taken along the line 12B—12B of FIG. 12.

FIG. 12C is a cross-sectional view of a portion of the heat exchange region taken along the line 12C—12C of FIG. 12.

DETAILED DESCRIPTION OF EMBODIMENTS

Figure 1:
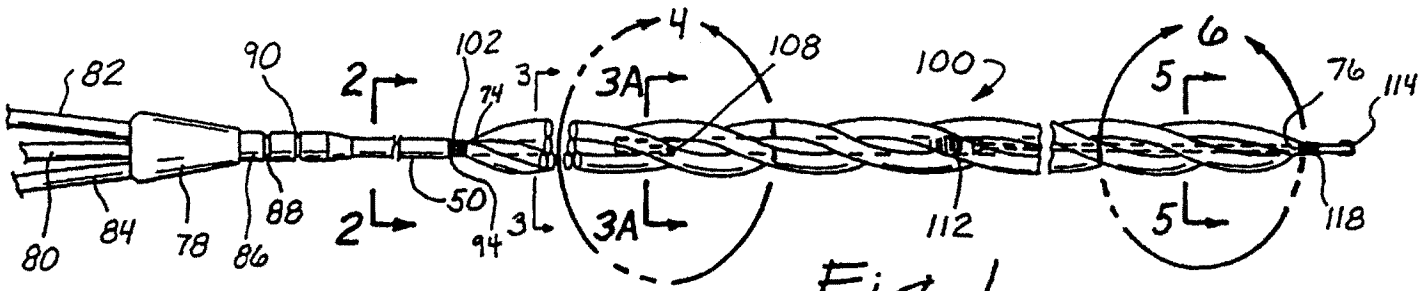
FIG. 1 is a perspective drawing of an embodiment of the catheter of the invention.
Figure 2:
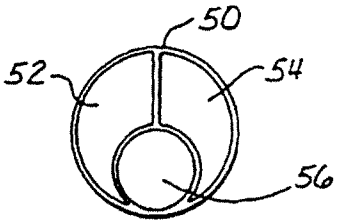
FIG. 2 is a cross-sectional drawing of the shaft of the catheter taken along the line 2—2 in FIG. 1.

The following detailed description is provided for the purpose of describing only certain embodiments or examples of the invention and is not intended to describe all possible embodiments and examples of the invention.

A. A Preferred Intravascular Heat Exchange Catheter System Useable To Perform the Methods of This Invention Referring to FIGS. 1 through 10A, in one embodiment, the catheter is comprised of a shaft 50 with a heat exchange region 100 thereon. The shaft has two roughly parallel lumens running through the proximal shaft, an inflow lumen 52 and an outflow lumen 54. The shaft generally also comprises a working lumen 56 running therethrough for the insertion of a guide wire, or the application of drugs, radiographic dye, or the like to the distal end of the catheter. The heat exchange region comprises a four-lumen balloon, with three outer lumens 58, 60, 62 disposed around an inner lumen 64 in a helical pattern. In the particular embodiment shown, the balloon preferably makes one full rotation about the inner lumen 64 for each 2 to 4 inches of length. All four lumens 58, 60, 62 and 64 are thin walled balloons and each outer lumen 58, 60, 62 shares a common thin wall segment 66, 68, 70 with the inner lumen. The balloon is approximately twenty-five centimeters long, and when inflated has an outer circumference 72 of approximately 0.328 in. When deflated, the profile is generally about 9 French (3 French is 1 mm in diameter). When the balloon portion is installed on the shaft, both the proximal end 74 of the balloon and the distal end 76 of the balloon are sealed around the shaft in fluid tight seals, as described more fully herebelow. Heat exchange fluid may be directed in through the inflow lumen, return through the outer lobes of the balloon in heat exchange proximity with blood flowing over the outside of the balloon, and then out through the outflow lumens, as will be described in greater detail below.

Figure 1A:
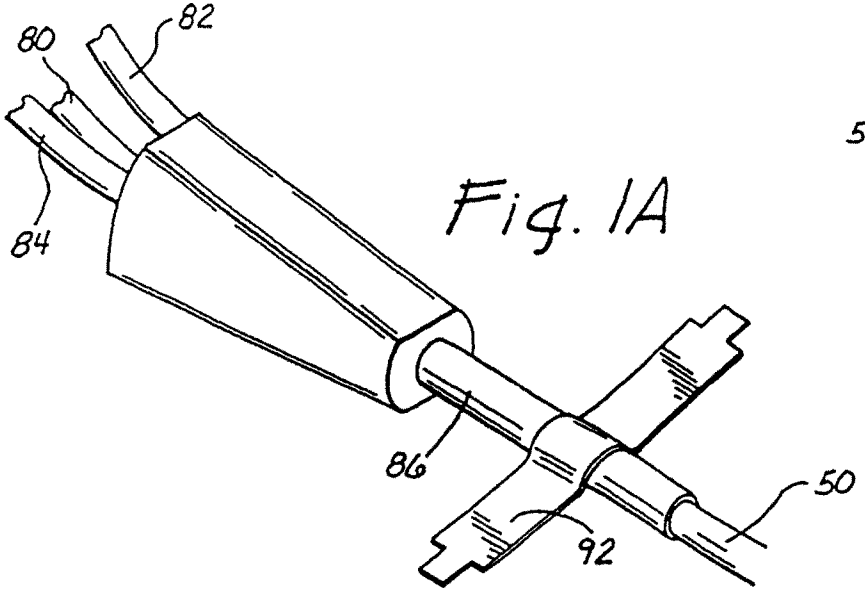
FIG. 1A is a perspective drawing of an alternative tie-down at the proximal end of the catheter shown in FIG. 1.
Figure 6:
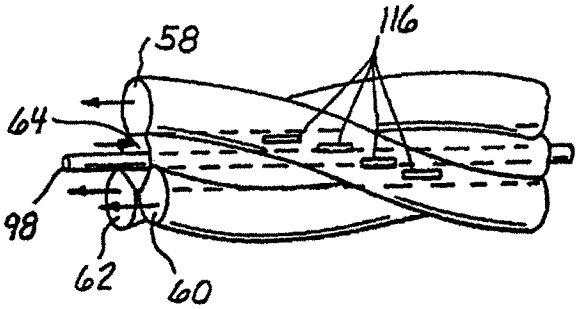
FIG. 6 is a perspective drawing of a segment of the heat exchange region of the catheter within the circle 6—6 in FIG. 1.
Figure 7:
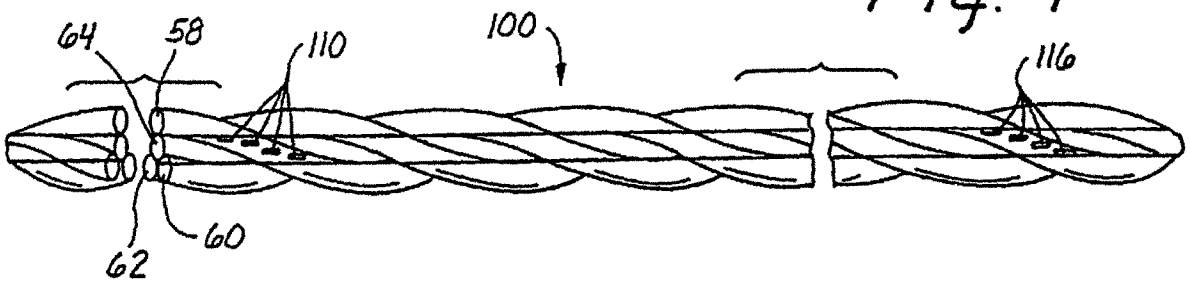
FIG. 7 is a perspective drawing of the multi-lobed balloon of one embodiment of the invention.
Figure 9:
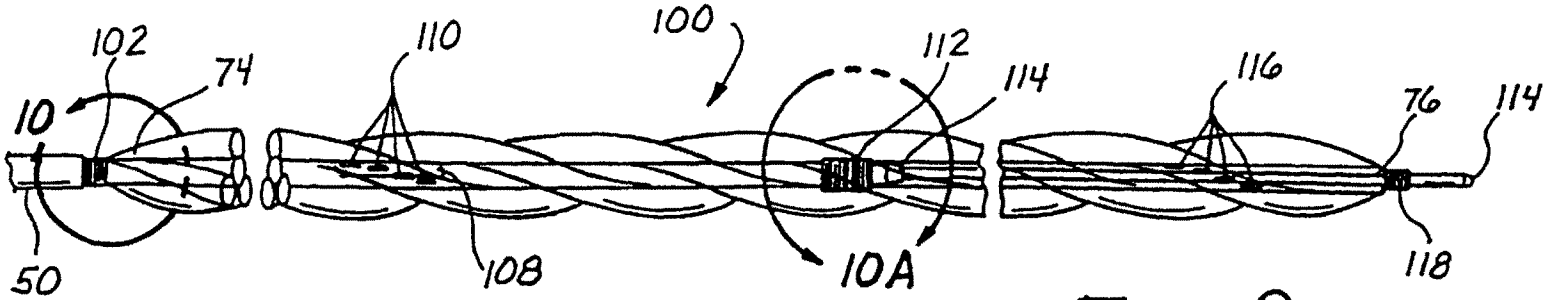
FIG. 9 is a perspective drawing of the heat exchange region formed by the shaft and multi-lobed balloon of FIGS. 7 and 8.

The catheter is attached at its proximal end to a hub 78. At the hub, the guide wire lumen 56 communicates with a guide wire port 80, the inflow lumen 52 is in fluid communication with an inflow port 82, and the outflow lumen 54 is in communication with an outflow port 84. Attached at the hub and surrounding the proximal shaft is a length of strain relief tubing 86 which may be, for example, a length of heat shrink tubing. The strain relief tubing may be provided with suture tie- downs 88, 90. Alternatively, a butterfly tie-down 92 may be provided. (See FIG. 1A).

Between the strain relief tubing 86 and the proximal end of the balloon 74, the shaft 50 is extruded with an outer diameter of about 0.118 inches. The internal configuration is as shown in cross-section in FIG. 2. Immediately proximal of the balloon attachment 74, the shaft is necked down 94. The outer diameter of the shaft is reduced to about 0.100 to 0.110 inches, but the internal configuration with the three lumens is maintained. Compare, for example, the shaft cross-section of FIG. 2 with the cross-section of the shaft shown in FIG. 3. This length of reduced diameter shaft remains at approximately constant diameter of about 0.100 to 0.110 inches between the necked down location at 94 and a distal location 96 where the outflow lumen is sealed and the guide wire extension tube 98 is attached as will be described.

At the necked down location 94, a proximal balloon marker band 102 is attached around the shaft. The marker band is a radiopaque material such as a platinum or gold band or radiopaque paint, and is useful for locating the proximal end of the balloon by means of fluoroscopy while the catheter is within the body of the patient.

At the location marked by the marker band, all four lobes of the balloon are reduced down and fastened around the inner member 67 in a fluid-tight seal. This may be accomplished by folding the outer lobes of the balloon 58, 60, 62 down around the inner lumen 64, placing a sleeve, for example a short length of tubing, snugly over the folded-down outer lumens of the balloon and inserting adhesive, for example by wicking the adhesive, around the entire inner circumference of the sleeve. The inner lumen is then fastened to the shaft using a second short length of tubing. The second short length for example 1 mm, of intermediate tubing 104 is heat welded to the inside of the inner lumen. The intermediate tube has an outer diameter approximately the same as the inner diameter of the inner lumen. The intermediate tube is then slid over the shaft at about the location of the neck-down region near the proximal marker 102, and adhesive 106 is wicked into the space between the inside of the intermediate tubing and the outer surface of the shaft 50. A similar process may be used to attach the distal end of the balloon, as will be described, except that the distal end of the balloon is attached down around the guide wire extension tube 98 rather than the shaft.

Just distal of the proximal balloon seal, under the balloon within the inner lumen, an elongated window 108 is cut through the wall of the outflow lumen in the shaft. Along the proximal portion of the balloon above this window, five slits, e.g. 110, are cut into the common wall between each of the outer lumens 58, 60, 62 and the inner lumen 64. Because the outer lumens are twined about the inner lumen in a helical fashion, each of the outer tubes passes over the outflow lumen of the inner shaft member at a slightly different location along the length of the inner shaft and, therefore, an elongated window 108 is cut into the outflow lumen of the shaft so that each outer lumen has at least one slit e.g. 110 that is located over the window in the shaft. Additionally, there is sufficient clearance between the outer surface of the shaft and the wall of the inner lumen to allow relatively unrestricted flow of heat exchange fluid through all 5 slits in each outer lumen, around the shaft, and through the elongate window 108 into the outflow lumen 54 in the shaft 50.

Figure 10:
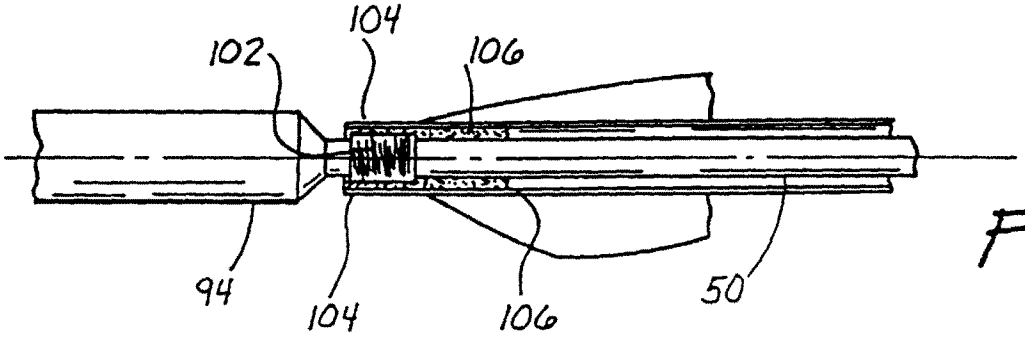
FIG. 10 is an expanded view of the attachment of the central lumen of the balloon to the shaft of the catheter of FIG. 9 showing the region within the circle 10—10 in FIG. 9.
Figure 10A:
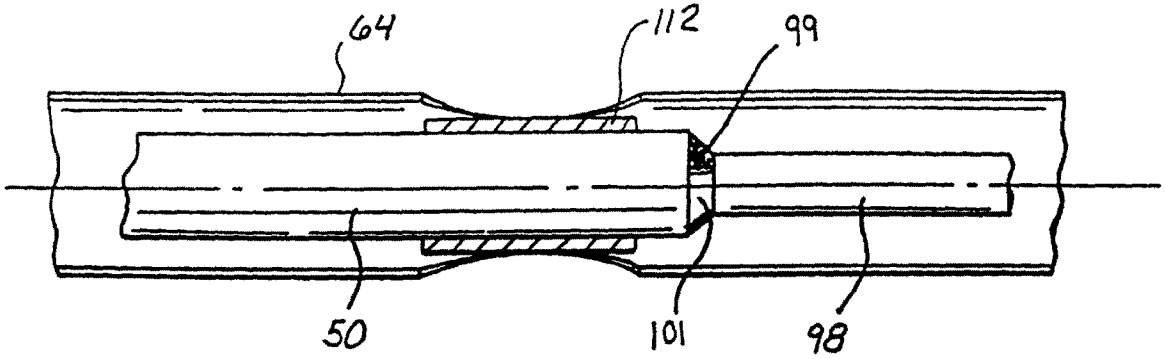
FIG. 10A is an expanded view of the plug between the shaft and the central lumen of the balloon of the catheter of FIG. 9 showing the region within the circle 10A—10A in FIG. 9.

Distal of the elongated window in the outflow lumen, the inner lumen 64 of the four-lumen balloon is sealed around the shaft in a fluid tight plug. Referring to FIG. 10a, the plug is formed by, for example shrinking a relatively thick length of PET tubing to form a length of plug tubing 112 where the inner diameter of the length of plug tubing is approximately the same as the outer diameter of the shaft at the location where the plug is to be formed. The plug tubing is slid over the shaft and fits snugly against the shaft. The shaft is generally formed of a material that is not heat shrinkable. As may be seen in FIG. 10A and FIG. 3, some clearance exists between the outer wall of the shaft and the inner wall of the inner lumen 64. The walls of the inner lumen are composed of thin heat shrinkable material, for example PET. A probe with a resistance heater on the distal end of the probe is inserted into the guide wire lumen of the shaft and located with the heater under the plug tubing. The probe is heated, causing the heat shrink wall of the inner lumen to shrink down against the plug tubing, and the plug tubing to shrink slightly down against the shaft. The resultant mechanical fit is sufficiently fluid tight to prevent the outflow lumen and the space between the shaft and the wall of the inner lumen from being in fluid communication directly with the inner member or the inflow lumen distal of the plug except through the outer lumens as will be detailed below.

Just distal of the plug, the outflow lumen is closed by means of a heat seal 99, and the inflow lumen is skived to form an opening 101 to the inner member. This may be accomplished by necking down the shaft at 96, attaching a guide wire extension tube 98 to the guide wire lumen, and simultaneously opening the inflow lumen 101 to the interior of the inner lumen and heat sealing the outflow lumen shut 101. The guide wire extension tube continues through the inner lumen, beyond the distal seal of the balloon (described below) to the distal end of the catheter 114 and thereby creates communication between the guide wire port 80 and the vessel distal of the catheter for using a guide wire to place the catheter or for infusing drugs, radiographic dye, or the like beyond the distal end of the catheter.

The distal end of the balloon 76 is sealed around the guide wire extension tube in essentially the same manner as the proximal end 74 is sealed down around the shaft. Just proximal of the distal seal, five slits 116 are cut into the common wall between each of the three outer lumens 58, 60 62 of the balloon and the inner lumen 64 so that each of the outer lumens is in fluid communication with the inner lumen.

Just distal of the balloon, near the distal seal, a distal marker band 118 is placed around the guide wire extension tube. A flexible length of tube 120 may be joined onto the distal end of the guide wire tube to provide a soft tip to the catheter as a whole.

In use, the catheter is inserted into the body of a patient so that the balloon is within a blood vessel, for example in the inferior vena cava (IVC). Heat exchange fluid is circulated into the inflow port 82, travels down the inflow lumen 52 and into the inner lumen 64 distal of the plug tube 112. The heat exchange fluid fills the inner lumen and travels down the inner lumen, thence through slits 116 between the inner lumen 64 and the three outer lumens 58, 60, 62.

The heat exchange fluid then travels back through the three outer lumens of the balloon to the proximal end of the balloon. Since outer lumens are wound in a helical pattern around the inner lumen, at some point along the length of the balloon near the proximal end and proximal of the plug, each outer lumen is located over the portion of the shaft having the window to the outflow lumen 108. There is also sufficient clearance between the wall of the inner lumen and the shaft, as illustrated in FIG. 3, that even the slits that are not directly over the window 108 allow fluid to flow into the space between the wall of the inner lumen and the outer wall of the shaft 50 and then through the window 108 and into the outflow lumen. The heat exchange fluid then flows down the outflow lumen and out the outflow port 84. At a fluid pressure of 41 pounds per square inch, flow of as much as 500 milliliters per minute may be achieved with this design.

Counter-current circulation between the blood and the heat exchange fluid is highly desirable for efficient heat exchange between the blood and the heat exchange fluid. Thus if the balloon is positioned in a vessel where the blood flow is in the direction from proximal toward the distal end of the catheter, for example if it were placed from the femoral vein into the Inferior Vena Cava (IVC) cava, it is desirable to have the heat exchange fluid in the outer balloon lumens flowing in the direction from the distal end toward the proximal end of the catheter. This is the arrangement described above. It is to be readily appreciated, however, that if the balloon were placed so that the blood was flowing along the catheter in the direction from distal to proximal, for example if the catheter was placed into the IVC from a jugular insertion, it would be desirable to have the heat exchange fluid circulate in the outer balloon lumens from the proximal end to the distal end. Although in the construction shown this is not optimal and would result is somewhat less effective circulation; this could be accomplished by reversing which port is used for inflow direction and which for outflow.

Where heat exchange fluid is circulated through the balloon that is colder than the blood in the vessel into which the balloon is located, heat will be exchanged between the blood and the heat exchange fluid through the outer walls of the outer lumens, so that heat is absorbed from the blood. If the temperature difference between the blood and the heat exchange fluid (sometimes called "ΔT"), for example if the blood of the patient is about 37° C. and the temperature of the heat exchange fluid is about 0° C., and if the walls of the outer lumens conduct sufficient heat, for example if they are of very thin (0.002 inches or less) plastic material such as polyethylene terephthalate (PET), enough heat may be exchanged (for example about 200 watts) to lower the blood temperature sufficiently to effect hypothermic anti-platelet activity, and to cool the temperature downstream of the catheter, for example of the heart, sufficiently for therapeutic inhibition of platelet activation, aggregation and/or adhesion. If the cooling catheter is left in place long enough for example for over half an hour, the entire body temperature of the patient may be cooled sufficiently for hypothermic anti-platelet activity. In this way, for example, blood to the brain and even the brain tissue itself may be cooled sufficiently for therapeutic hypothermic anti-platelet effect.

The helical structure of the outer lumens has the advantage over straight lumens of providing greater length of heat exchange fluid path for each length of the heat exchange region. This creates additional heat exchange surface between the blood and the heat exchange fluid for a given length of balloon. It may also provide for enhanced flow patterns for heat exchange between flowing liquids. The fact that the heat exchange region is in the form of an inflatable balloon also allows for a minimal insertion profile, for example 9 French or less, while the heat exchange region may be inflated once inside the vessel for maximum diameter of the heat exchange region in operation.

Automated control of the process is optional. Examples of apparatus and techniques that may be used for automated control of the process are described in U.S. pat. Nos. 6,149,673 and 6,149,676 and co-pending U.S. patent application Ser. No. 09/138,830, the entireties of which are expressly incorporated herein by reference.

Referring now to FIGS. 11 through 13B, in another example of a preferred embodiment, the heat exchange region is in the form of a series of five lumens arranged side-by-side in a configuration that may be loosely described as a twisted ribbon. The heat transfer fluid circulates to and from the heat exchange region 202 via channels formed in the shaft 206 in much the same manner as previously described for shaft 50. Indeed, although not depicted, the shaft has a similar internal configuration as the shaft previously described with an inflow lumen, an outflow lumen, and a working lumen. Although also not depicted, a hub is attached at the proximal end of the shaft which is maintained outside the body; the hub has a guide wire port communicating with the working lumen, an inflow port communicating with the inflow lumen, and an outflow port communicating with the outflow lumen. Heat exchange fluid is directed into the catheter through the inflow port and removed from the catheter through the outflow port. A guide wire, or alternatively medicaments, radiographic fluid or the like are introduced through the guide wire port and may thus be directed to the distal end of the catheter.

Figure 11:
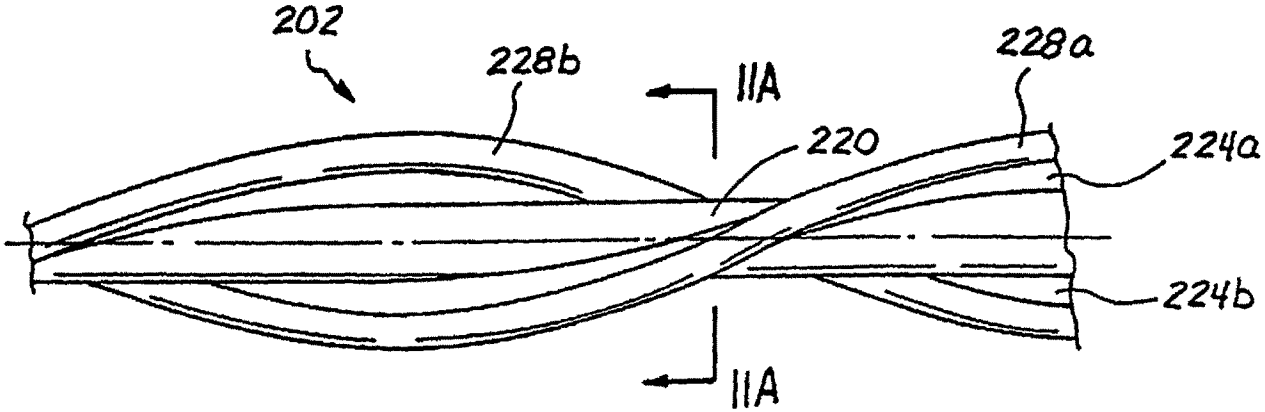
FIG. 11 is a perspective view of a portion of a multi-lobed, curvilinear heat exchange balloon that forms a portion of one embodiment of the invention.

FIGS. 11 and 11A illustrate this embodiment of a heat exchange region 202 comprising a plurality of tubular members that are stacked in a helical plane. More specifically, a central tube 220 defines a central lumen 222 therewithin. A pair of smaller intermediate tubes 224a, 224b attaches to the exterior of the central tube 220 at diametrically opposed locations. Each of the smaller tubes 224a, 224b defines a fluid lumen 226a, 226b therewithin. A pair of outer tubes 228a, 228b attaches to the exterior of the intermediate tubes 224a, 224b in alignment with the aligned axes of the central tube 220 and intermediate tubes 224a, 224b. Each of the outer tubes 228a, 228b defines a fluid lumen 230a, 230b within. By twisting the intermediate and outer tubes 224a, 224b, 228a, 228b around the central tube 220, the helical ribbon-like configuration of FIG. 11 is formed.

Now with reference to FIGS. 12 and 12A-12C, a proximal manifold of the heat exchange region 202 will be described. The shaft 206 extends a short distance, desirably about 3 cm, within the central tube 220 and is thermally or adhesively sealed to the interior wall of the central tube as seen at 250. As seen in FIG. 12A, the shaft 206 includes a planar bulkhead or web 252 that generally evenly divides the interior space of the shaft 206 into an inflow lumen 254 and an outflow lumen 256. A working or guide wire lumen 260 is defined within a guide wire tube 262 that is located on one side of the shaft 206 in line with the bulkhead 252. Desirably, the shaft 206 is formed by extrusion. The outflow lumen 256 is sealed by a plug 264 or other seal at the terminal end of the shaft 206. The inflow lumen 254 remains open to the central lumen 222 of heat exchange region 202. The guide wire tube 262 continues a short distance and is heat bonded at 270 to a guide wire extension tube 272 generally centered within the central tube 220.

A fluid circulation path is illustrated by arrows in FIG. 12 and generally comprises fluid passing distally through the inflow lumen 254 and then through the entirety of the central lumen 222. The heat exchange fluid is directed from the central lumen 222 to the intermediate and outer tubes as will be described below, and returns through the lumens 226a, 226b, and 230a, 230b of the intermediate and outer tubes 224a, 224b, and 228a, 228b, respectively, and enters reservoirs 274 and 275. Alternatively, two windows may be formed 276 and a counterpart not shown in FIG. 12 one helical twist farther down the shaft, between each side of the twisted ribbon (i.e., lumens 224a and 224b on one side, and 228a and 228b on the other side). In this way, one reservoir from each side of the twisted ribbon is formed in fluid communication with the outflow lumen 256 (configuration not shown). Fluid then enters the outflow lumen 256 through apertures, e.g., 276, provided in the central tube 220 and a longitudinal port 278 formed in the wall of the shaft.

Figure 13:
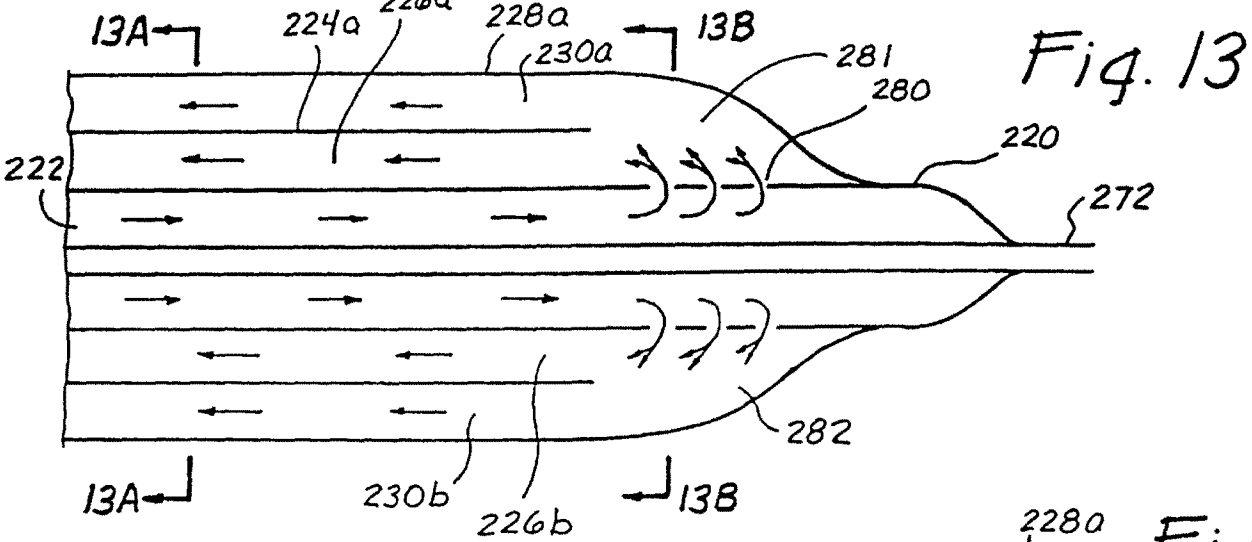
FIG. 13 is a sectional view of the distal portion of the heat exchange region of one embodiment of the invention.
Figure 13B:
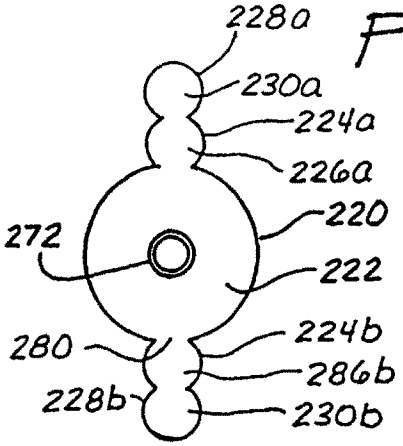
FIG. 13B is a cross-sectional view of a portion of the heat exchange region taken through line 13B—13B FIG. 13.
Figure 13A:
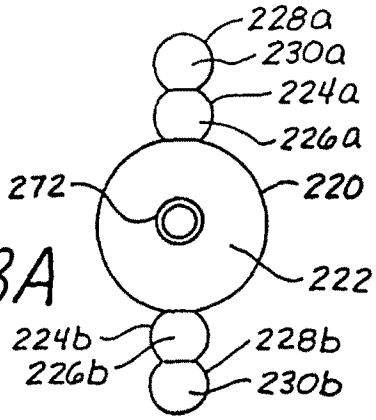
FIG. 13A is a cross-sectional view of a portion of the heat exchange region taken through line 13A—13A of FIG. 13.

A distal manifold of the heat exchange region 202 is shown and described with respect to FIGS. 13 and 13A-13B. The outer tubes 228a, 228b taper down to meet and seal against the central tube 220 which, in turn, tapers down and seals against the guide wire extension tube 272. Fluid flowing distally through the central lumen 222 passes radially outward through a plurality of apertures 280 provided in the central tube 220. The apertures 280 open to a distal reservoir 282 in fluid communication with lumens 226a, 226b, and a distal reservoir 281 in fluid communication with lumens 230a, 230b of the intermediate and outer tubes 224a, 224b, and 228a, 228b.

With this construction, heat exchange fluid [introduced into the input port 240 will] circulates through the inflow lumen 254, into the central lumen 222, out through the *inflow lumen 254, into the central lumen 222, out through the* apertures 280, and into the distal reservoir 282. From there, the heat exchange fluid will travel proximally through both intermediate lumens 226a, 226b and outer lumens 230a, 230b to the proximal reservoirs 274 and 275. Fluid then passes radially inwardly through the apertures 276 and port 278 into the outflow lumen 256. Then the fluid circulates back down the shaft 206 and out [the] *of an* outlet port [242].

The ribbon configuration of FIGS. 11-13B is advantageous for several reasons. First, the relatively flat ribbon does not take up a significant cross-sectional area of a vessel into which it is inserted. The twisted configuration further prevents blockage of flow through the vessel when the heat exchange region 202 is in place. The helical configuration of the tubes 224a, 224b, 228a, 228b also aids to center the heat exchange region 202 within a vessel by preventing the heat exchange region from lying flat against the wall of the vessel along any significant length of the vessel. This maximizes heat exchange between the lumens and the blood flowing next to the tubes. Because of these features, the twisted ribbon configuration is ideal for maximum heat exchange and blood flow in a relatively small vessel such as the carotid artery. As seen in FIG. 11A, an exemplary cross-section has a maximum diameter *300* of about 5 mm, permitting treatment of relatively small vessels. The helical pattern of the balloon in the fluid flow may act to induce a gentle mixing action of the flowing blood to enhance heat exchange between the heat exchange surface and the blood without inducing hemolytic damage that would result from more violent churning action.

The deflated profile of the heat exchange region is small enough to make an advantageous insertion profile, as small as 7 French for some applications. Even with this low insertion profile, the heat exchange region is efficient enough to adequately exchange heat with blood flowing past the heat exchange region to alter the temperature of the blood sufficient for anti-platelet action and affect the temperature of tissue downstream of the heat exchange region. Because of its smaller profile, it is possible to affect the temperature of blood in smaller vessels and thereby provide treatment to more localized body areas.

Figure 14:
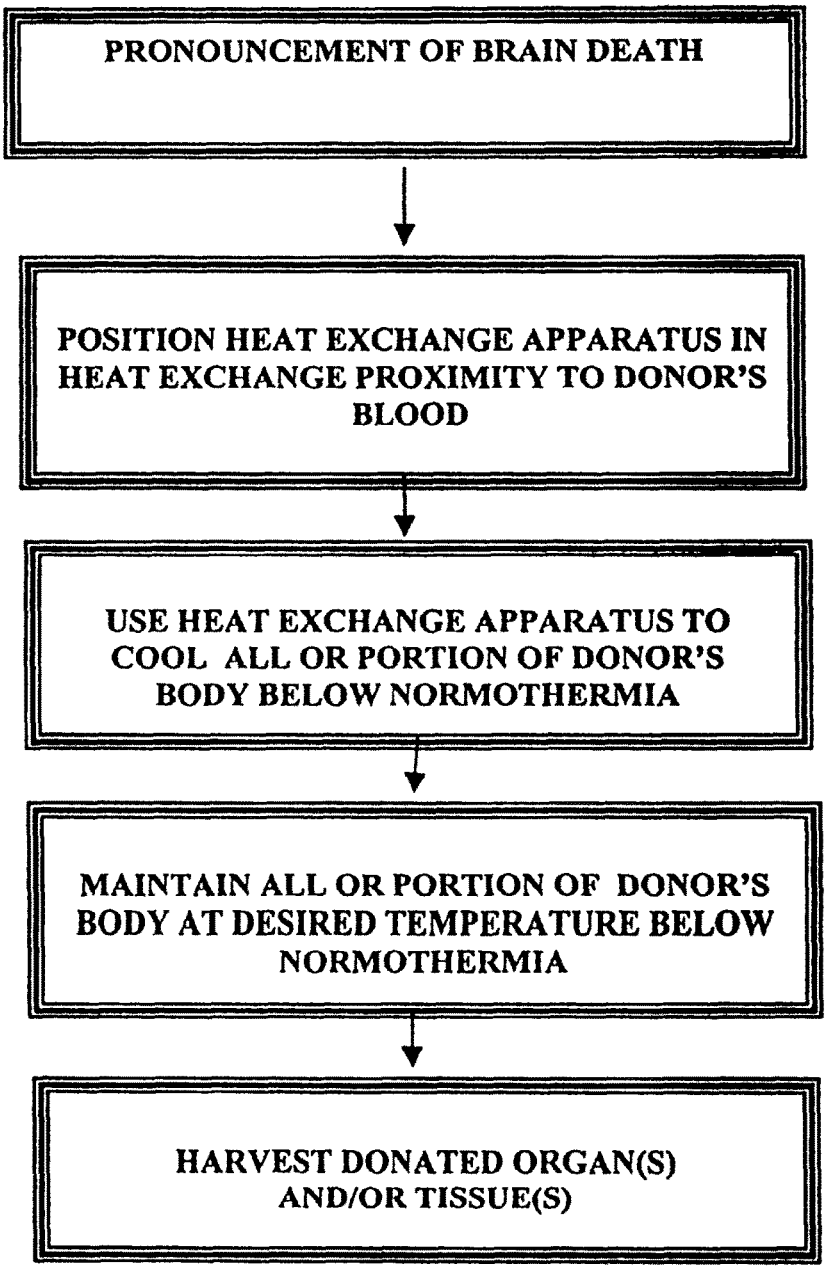
FIG. 14 is a general flow diagram of a method of the present invention wherein endovascular hypothermia is used in a beating heart organ dead donor to minimize the likelihood of hypoxic damage to the donor's organs between the time the donor is pronounced brain dead and the time the organs are actually harvested from the donor's body.
Figure 15:
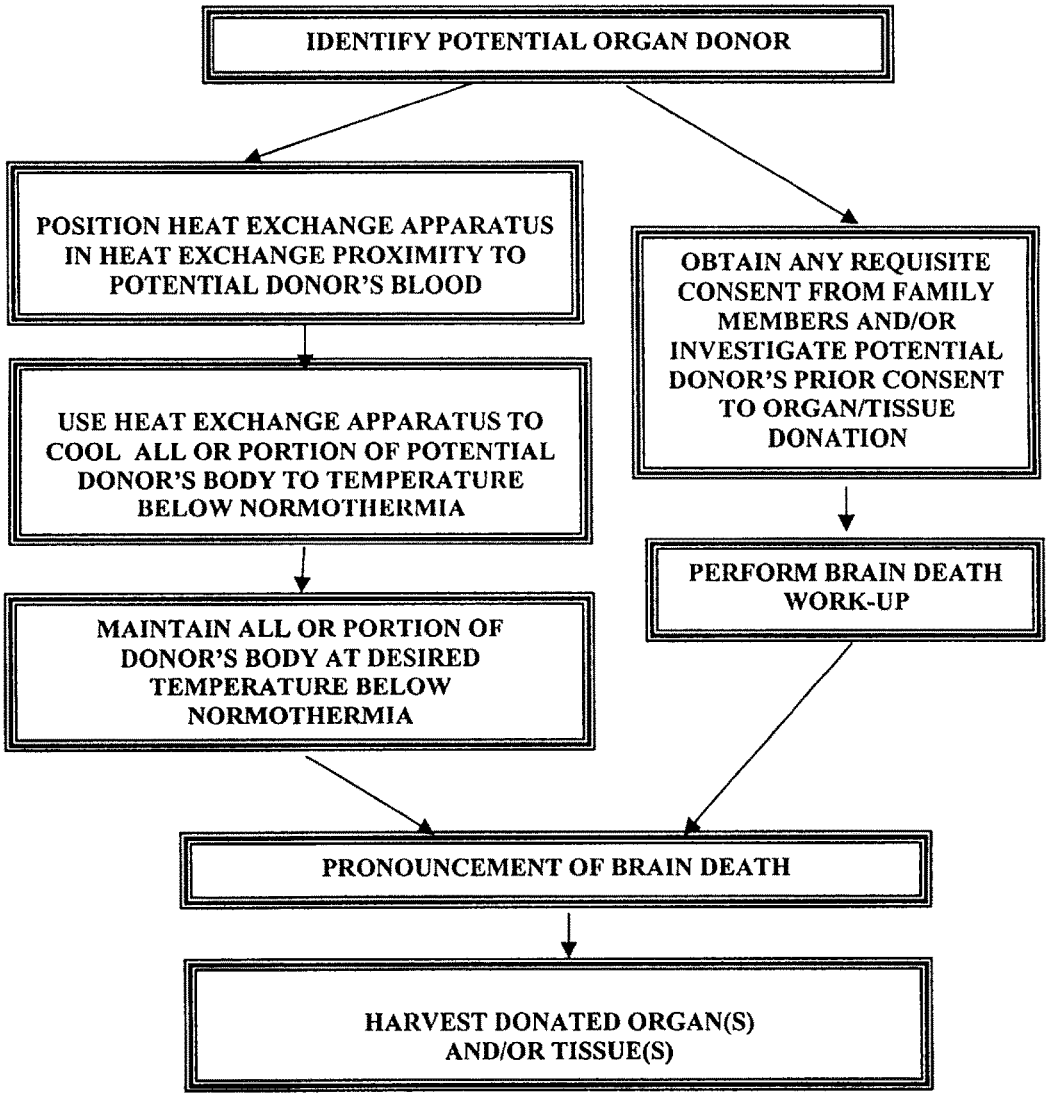
FIG. 15 is a general flow diagram of a method of the present invention wherein endovascular hypothermia is used in a beating heart but brain dead organ donor to minimize the likelihood of hypoxic damage to the donor's organs from the time brain death is suspected to have occurred, during the time the brain death work-up is performed and until the organs are actually harvested from the donor's body.
Figure 16:
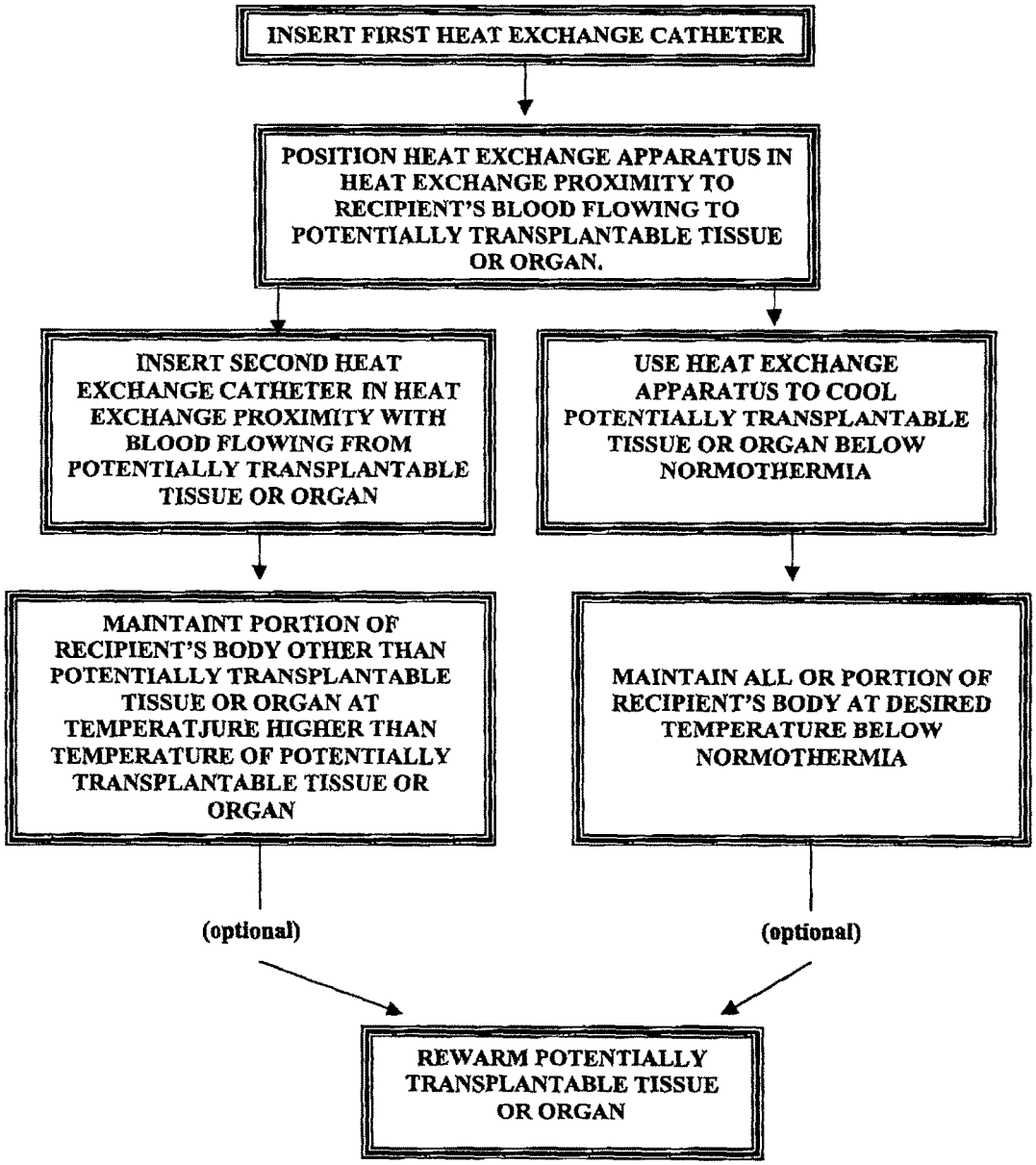
FIG. 16 is a general flow diagram of the present invention wherein endovascular hypothermia is used in a beating heart but brain dead organ donor to cool potentially transplantable organs or tissue while simultaneously maintaining other tissue at a higher temperature.

This configuration has a further advantage when the heat exchange region is placed in a tubular conduit such as a blood vessel, especially where the diameter of the vessel is approximately that of the major axis (width) of the cross section of the heat exchange region. The configuration tends to cause the heat exchange region to center itself in the middle of the vessel. This creates two roughly semicircular flow channels within the vessel, with the blood flow channels divided by the relatively flat ribbon configuration of the heat exchange region. It has been found that the means for providing maximum surface for heat exchange while creating minimum restriction to flow is this configuration, a relatively flat heat exchange surface that retains two approximately equal semi-circular cross-sections. This can be seen in reference to FIG. 11A if the functional diameter of the dashed circle 300 is essentially the same as the luminal diameter of a vessel into which the twisted ribbon is placed. Two roughly semi-circular flow paths 302, 304 are defined by the relatively flat ribbon configuration of the heat exchange region, i.e. the width or major axis (from the outer edge of 228a to the outer edge of 228b) is at least two times longer than the height, or minor axis (in this example, the diameter of the inner tube 222) of the overall configuration of the heat exchange region. It has been found that if the heat exchange region occupies no more than about 50% of the overall cross-sectional area of the circular conduit, a highly advantageous arrangement of heat exchange to flow is created. The semi-circular configuration of the cross-section of the flow channels is advantageous in that, relative to a round cross-sectioned heat exchange region (as would result from, for example, a sausage shaped heat exchange region) the flow channels created minimize the surface to fluid interface in a way that minimizes the creation of laminarflow and maximizes mixing. Maximum blood flow is important for two reasons. The first is that flow downstream to the tissue is important, especially if there is obstruction in the blood flow to the tissue. The second reason is that heat exchange is highly dependent on the rate of blood flow past the heat exchange region, with the maximum heat exchange occurring with maximum blood flow, so maximum blood flow is important to maximizing heat transfer. B. Examples of Methods for Preventing Hypoxic Damage to Organs and Tissues in a Beating Heart Organ Donor:

FIGS. 14, 15 and 16 are flow diagrams that illustrate examples of methods wherein endovascular hypothermia is used in beating heart organ donors, prior to the harvesting of organs and/or tissues for transplantation, in order to decrease the potential for hypoxic damage to the transplantable organs and tissues in the event of an hypoxic episode. The types of hypoxic episodes that may occur in beating heart organ donors include; cardiac arrest, ventricular arrhythmia, periods of hypotension, disruption of ventilation due to inadvertent disconnection of ventilator tubing, hypoxia secondary to pulmonary embolus, etc.

In the example of FIG. 14, the endovascular hypothermia is initiated in an organ donor after the organ donor has been formally declared or pronounced brain dead. In the example of FIG. 15, the endovascular hypothermia is initiated in an organ donor who is suspected to be brain dead but who has not yet been declared or pronounced brain dead, and such hypothermia is maintained while the potential donor is subjected to the tests and evaluations necessary to make a clinical determination of brain death.

Additionally, even after the declaration or pronouncement of brain death has been made, there may be substantial further delays before the organs or tissues can be harvested from the donor's body. This is especially true in cases where a time-critical organ such as the heart has been matched to a recipient who is located far away from the donor and it is necessary to wait until a surgical team has been flown in from the recipient's location to perform the organ harvest and to then transport the critical organ to the location where the transplant surgery is to be conducted. Accordingly, in such cases, the provision of endovascular hypothermia even after the brain death declaration or pronouncement has been made may be beneficial in avoiding hypoxic damage to donor's the organs or tissues.

Moreover, a substantial period of time may be required before the brain death declaration or pronouncement may be made, as it is often necessary for heath care workers to locate and obtain written consent from the donor's family and to perform extensive tests and evaluations to confirm that the donor is in fact brain dead. The exact criteria by which brain death may be declared or pronounced may differ from state to state, country to country, or even institution to institution. In many jurisdictions, a declaration or pronouncement of brain death can only be made after numerous tests and evaluations have been completed (collectively referred to herein as the "brain death work-up"). These required tests and evaluations may include a clinical assessment to establish the lack of neurological responses and reflexes, hypoxia test(s) to confirm that the spontaneous respiratory drive is absent, and multiple electroencephalograms (EEGs) taken at time points separated by a prescribed waiting period (e.g., 24 hours). In at least some institutions, the declaration or pronouncement of brain death must be made by no fewer than two (2) physicians. Thus, the time period required to obtain the requisite consent and complete the entire brain death work up may span 48 hours or even longer. The provision of endovascular hypothermia during the brain death work up period in accordance with the method of FIG. 15 may be extremely beneficial in such cases to, for example, protect potential donor organs and tissue.

Specifically referring to the method of FIG. 14, in a case where the potential organ donor has already been declared or pronounced brain dead in accordance with the applicable criteria, an endovascular heat exchange apparatus is inserted into the patient's vasculature and used to cool blood flowing though the vasculature such that all or a portion of the donor's body is cooled to a temperature below 37° C. (i.e., below normothermia). In many cases, the desired temperature will be in the range of about 34° C. through about 28° C. and preferably about 30° C. Generally the lower the temperature, the more protective it is of the donor organs or tissue, but below a temperature of about 25° C. the heart function may be adversely affected. In order to accomplish endovascular hypothermia, the heart must generally be pumping effectively, so a body temperature of about 30° C. will effectively protect the organ or tissue for preservation and at the same time, will not adversely affect cardiac function. The endovascular heat exchange device may comprise a catheter of the type shown in FIGS. 1-13C and described hereabove. The endovascular heat exchange device may further be used in conjunction with a controller and/or related equipment useable to monitor and control the temperature of the catheter and/or the patient. Examples of heat exchange catheters and related devices & controllers that might be useable in this step of the method are described in PCT International Application No. PCT/US99/18939 and U.S. Pat. Nos. 5,486,208 (Ginsburg), 6,149,676 (Ginsburg), 6,149,673 (Ginsburg), 5,957,963 (Dobak III), 6,096,608 (Dobak III, et al.), 6,110,168 (Ginsburg), 6,126,684(Gobin, et al.) and 6,264,679 (Keller, et al.), the entire disclosures of which expressly incorporated herein by reference. In particular, one presently preferred intravascular heat exchange catheter system for use in the present invention is described in U.S. application Ser. No. 09/777,612 the entirety of which is expressly incorporated herein by reference and portions of which are set forth in the paragraphs herebelow. In cases where it is desired to cool the donor's entire body such that the donor's core body temperature is in the desired range, the endovascular temperature exchange device may be positioned in the inferior vena cava near the right atrium of the donor's heart such that venous blood that is cooled by the heat exchange apparatus will subsequently be pumped throughout the donor's body by the donor's the heart, cooling the entire body in the process. In other cases where it is desired to selectively cool only a specific body portion (e.g., a limb, organ or group of organs) to a temperature within the desired target range, the heat exchange apparatus may be positioned within a blood vessel through which blood flows into the specific body portion (e.g., a limb, organ or group of organs) and that heat exchange apparatus may then be used to cool blood flowing into the specific organ or specific portion of the body, thereby also cooling the parenchyma of that specific organ or specific portion of the body to the desired target temperature. A temperature monitoring probe or thermocouple may be placed within the specific body portion (e.g., a limb, organ or group of organs) to facilitate the controlled cooling of that specific body portion (e.g., a limb, organ or group of organs) to the desired target temperature without significant over-shoot and to thereafter maintain the specific body portion (e.g., a limb, organ or group of organs) at the target temperature for the desired period of time. Some incidental cooling of other portions of the body may or may not occur concurrently with the selective cooling of the specific body portion (e.g., a limb, organ or group of organs) to the desired target temperature and subsequent maintenance of that target temperature.

In cases where it is desired to minimize or prevent cooling of portions of the body other than the selected body portion (e.g., a limb, organ or group of organs), a second heat exchange apparatus may be placed in one or more other blood vessels from which blood flows out of or away from the selected body portion (e.g., a limb, organ or group of organs) and the second heat exchange apparatus may be used to rewarm blood that flows out of or away from the selected body portion (e.g., a limb, organ or group of organs or blood flowing from the heart), thereby preventing the remainder of the body or at least the heart from becoming as hypothermic as the tissue or organ desired for transplantation. In this manner it is possible to cool the organ or tissue for transplantation well below the 25° C. temperature at which the heart begins to experience fibrillation or other adverse events, and yet keep the heart above that temperature to maintain effective cardiac function. For example, a first, cooling catheter might be placed in the renal artery to cool a kidney and a second warming catheter be placed in the renal vein or the IVC to warm blood returning from the kidneys to the heart. In fact, several additional catheters might be used, for example a cooling catheter might be placed in the artery for each kidney, and a warming catheter in each of the veins coming from the kidneys, and a warming catheter in IVC all to keep the heart warm enough to function effectively as a pump, and yet cool the target organ or tissue. This method of persevering organs or tissue is illustrated in the flow chart of FIG. 16.

Although several illustrative examples of means for practicing the invention are described above, these examples are by no means exhaustive of all possible means for practicing the invention. The scope of the invention should therefore be determined with reference to the appended claims, along with the full range of equivalents to which those clams are entitled.

What is claimed is:

[1. A method for preventing hypoxic damage to a potentially transplantable organ or tissue prior to explantation of the organ or tissue from the body of a mammalian donor; said method comprising the steps of:

a. placing an intravascular heat exchange apparatus within a blood vessel of the donor such that the donor's blood continues to circulate through that blood vessel and heat is exchanged between the circulating blood and the intravascular heat exchange apparatus; and, b. using the intravascular heat exchange apparatus to cool the donor's flowing blood, thereby lowering the donor's core body temperature to a temperature that is below normothermia.]

[2. A method according to claim 1 wherein Step a comprises inserting a heat exchange catheter having a heat exchange region into the vasculature of a donor and positioning the catheter such that blood flowing to at least the potentially transplantable organ or tissue passes within heat exchange proximity to the heat exchange region and wherein Step b comprises exchangeing heat with the blood that passes in heat exchange proximity to the heat exchange region for a period of time sufficient to cool at least the potentially transplantable organ or tissue to a temperature below normothermia.]

[3. A method according to claim 1 wherein performance of the method is begun before any declaration of donor brain death has been made.]

[4. A method according to claim 1 wherein performance of the method is begun after a declaration of donor brain death has been made.]

[5. A method according to claim 1 wherein the temperature is between approximately 30° C. and approximately 36° C.]

[6. A method according to claim 1 wherein the intravascular heat exchange device is an elongate flexible catheter having a heat exchange region formed on a portion of the catheter that becomes inserted into the donor's vasculature.]

[7. A method according to claim 6 wherein the heat exchange region of the catheter occupies less than the full length of the catheter portion that becomes inserted in the donor's vasculature.]

[8. A method according to claim 1 wherein the heat exchange apparatus is placed in the donor's venous vasculature.]

[9. A method according to claim 8 wherein the heat exchange apparatus is placed in the donor's vena cava.]

[10. A method according to claim 9 wherein the heat exchange apparatus is placed in the donor's inferior vena cava.]

[11. A method according to claim 9 wherein the heat so exchange apparatus is placed in the donor's superior vena cava.]

[12. A method according to claim 1 wherein the donor's entire body is cooled to a temperature below normothermia.]

[13. A method according to claim 1 wherein the core body temperature is cooled to a desired temperature below normothermia and the remainder of the donor's body is either hypothermic, normothermic or hyperthermic.]

[14. A method according to claim 13 wherein at least one raised area is formed on the heat exchange apparatus to increase its heat exchange surface area.]

[15. A method according to claim 14 wherein said raised area comprises a structure selected from the group consisting of a fin, a projection, a bulge, a hollow raised area and a solid raised area.]

[16. A method according to claim 1 wherein performance of the method is continued until explantation of the potentially transplantable organ or tissue.]

[17. A method according to claim 1 wherein the organ or tissue is selected from the group consisting of:

heart;
lung;
liver;
kidney;
nervous tissue;
tendon;
bone;
a limb;
a finger;
a toe;
skin;
cornea;
bone marrow; and,
intestine.]

[18. A method according to claim 1 further comprising the steps of:

monitoring the temperature of at least a portion of the donor's body and adjusting the heat exchange between the heat exchanger and the donor's blood to maintain the monitored temperature within a desired range. ]

[19. A method according to claim 1 wherein the heat exchange device comprises a heat exchanger through which heat exchange fluid is circulated.]

[20. A method according to claim 19 wherein said heat exchanger comprises a heat exchange balloon.]

[21. A method according to claim 20 wherein the balloon is a single-lobed balloon.]

[22. A method according to claim 20 wherein the balloon is a multi-lobed balloon.]

[23. A method according to claim 1 wherein the heat exchange apparatus comprises a heat exchanger that is metallic.]

[24. A method according to claim 1 wherein the heat exchange apparatus comprises a balloon catheter, the balloon catheter comprising a catheter shaft and a balloon located on the catheter shaft, the balloon functioning as a heat exchanger, said balloon having an interior space and an exterior surface, the exterior surface of the balloon being in heat exchange proximity to blood that flows past it, the shaft having an inflow lumen and an outflow lumen wherein the inflow lumen is in fluid communication with the interior space of said balloon and the outflow lumen is in fluid communication with the interior space of said balloon, and wherein heat exchange fluid is circulated into the balloon through the inflow lumen and out of the balloon through the outflow lumen.]

[25. A method according to claim 1 comprising the additional step of sensing the temperature of the donor, and adjusting the step of exchanging heat with the blood in response to the sensed temperature.]

[26. A method according to claim 25 wherein the temperature sensed is the temperature of the donor's blood at a location that is not within heat exchange proximity to the intravascular heat exchange apparatus.]

[27. A method according to claim 25 wherein the temperature sensed is the donor's body temperature as measured at the donor's tympanic membrane.]

[28. A method according to claim 25 wherein the temperature sensed is the donor's rectal temperature.]

[29. A method according to claim 25 wherein the temperature sensed is representative of the whole body temperature of the donor.]

[30. A method according to claim 25 comprising the additional steps of selecting a target temperature below normothermia and maintaining the temperature of at least the potentially transplantable tissue or organ at the target temperature after said target temperature has been reached.]

[31. A method according to claim 30 comprising the additional steps of adding heat when the sensed temperature is below the target temperature, and removing heat from the blood when the sensed temperature is above the target temperature.]

[32. A method as in claim 2 further comprising the steps of inserting a second heat exchange catheter in heat exchange proximity to the blood flowing away from the potentially transplantable organ or tissue to maintain at least a portion of the patient's body other than the potentially transplantable organ or tissue at a temperature different than the potentially transplantable organ or tissue.]

[33. A method as in claim 32 wherein the potentially transplantable organ or tissue is maintained at a temperature below 30° C. and the heart is maintained at a temperature at least as high as 30° C.]

[34. A method according to claim 32 wherein the potentially transplantable organ or tissue is selected from the group consisting of:

kidney;
lung;
liver;
nervous tissue;
tendon;
bone;
a limb;
a finger;
a toe;
skin;
cornea;
bone marrow; and,
intestine.]

[35. A method according to claim 1 wherein Step A comprises inserting a heat exchange catheter having a heat exchange region into the vasculature of a donor and positioning the catheter such that it exchanges heat with blood flowing to the heart to maintain the temperature of the heart above the temperature that which cardiac arrest or significant cardiac dysfunction occurs, and further including a second catheter positioned in the vasculature and exchanging heat with the blood after it has exited the heart and is flowing to the potentially transplantable organ or tissue to cool at least the potentially transplantable organ or tissue to a temperature below the temperature at which the heart is maintained.]

*36. A method for deterring rejection of a transplanted organ or tissue in a body of a mammalian transplant recipient, said method comprising the steps of:*

*a. placing an intravascular heat exchange apparatus within a blood vessel of the recipient such that the recipient's blood continues to circulate through that blood vessel and heat is exchanged between the circulating blood and the intravascular heat exchange apparatus; and,*

*b. using the intravascular heat exchange apparatus to cool the recipient's flowing blood, thereby lowering the recipient's core body temperature to a temperature that is below normothermia.*

*37. A method according to claim 36 wherein Step a comprises inserting a heat exchange catheter having a heat exchange region into the vasculature of the recipient and positioning the catheter such that blood flowing to at least the transplanted organ or tissue passes within heat exchange proximity to the heat exchange region and wherein Step b comprises exchanging heat with the blood that passes in heat exchange proximity to the heat exchange region for a period of time sufficient to cool at least the transplanted organ or tissue to a temperature below normothermia.*

*38. A method as in claim 37 further comprising the steps of inserting a second heat exchange catheter in heat exchange proximity to the blood flowing away from the transplanted organ or tissue to maintain at least a portion of the recipient's body other than the translanted organ or tissue at a temperature different than the organ or tissue.*

*39. A method according to claim 36 wherein the temperature is between approximately 30° C. and approximately 36° C.*

*40. A method according to claim 36 wherein the intravascular heat exchange apparatus is an elongate flexible catheter having a heat exchange region formed on a portion of the catheter that becomes inserted into the recipient's vasculature.*

*41. A method according to claim 40 wherein the heat exchange region of the catheter occupies less than the full length of the catheter portion that becomes inserted in the recipient's vasculature.*

*42. A method according to claim 36 wherein the heat exchange apparatus is placed in the recipient's venous vasculature.*

*43. A method according to claim 42 wherein the heat exchange apparatus is placed in the recipient's vena cava.*

*44. A method according to claim 43 wherein the heat exchange apparatus is placed in the recipient's inferior vena cava.*

*45. A method according to claim 44 wherein the heat exchange apparatus is placed in the recipient's superior vena cava.*

*46. A method according to claim 36 wherein the recipient's entire body is cooled to a temperature below normothermia.*

*47. A method according to claim 36 wherein the core body temperature is cooled to a desired temperature below normothermia and the remainder of the recipient's body is either hypothermic, normothermic or hyperthermic.*

*48. A method according to claim 36 wherein at least one raised area is formed on the heat exchange apparatus to increase its heat exchange surface area.*

*49. A method according to claim 36 wherein the organ or tissue is selected from the group consisting of:*

*heart;*
*lung;*
*liver;*
*kidney;*
*nervous tissue;*
*tendon;*
*bone;*
*a limb;*
*a finger;*
*a toe;*
*skin;*
*cornea;*
*bone marrow; and,*
*intestine.*

*50. A method according to claim 36 further comprising the steps of:*

*monitoring the temperature of at least a portion of the recipient's body and adjusting the heat exchange between the heat exchanger and the recipient's blood to maintain the monitored temperature within a desired range.*

*51. A method according to claim 36 wherein the heat exchange device comprises a heat exchanger through which heat exchange fluid is circulated.*

*52. A method according to claim 36 wherein said heat exchanger comprises a heat exchange balloon.*

*53. A method according to claim 36 wherein the heat exchange apparatus comprises a balloon catheter, the balloon catheter comprising a catheter shaft and a balloon located on the catheter shaft, the balloon functioning as a heat exchanger, said balloon having an interior space and an exterior surface, the exterior surface of the balloon being in heat exchange proximity to blood that flows past it, the shaft having an inflow lumen and an outflow lumen wherein the inflow lumen is in fluid communication with the interior space of said balloon and the outflow lumen is in fluid communication with the interior space of said balloon, and wherein heat exchange fluid is circulated into the balloon through the inflow lumen and out of the balloon through the outflow lumen.*

*54. A method according to claim 36 comprising the additional step of sensing the temperature of the recipient, and adjusting the step of exchanging heat with the blood in response to the sensed temperature.*

*55. A method according to claim 54 wherein the temperature sensed is the temperature of the recipient's blood at a location that is not within heat exchange proximity to the intravascular heat exchange apparatus.*

*56. A method according to claim 54 wherein the temperature sensed is the recipient's body temperature as measured at the recipient's tympanic membrane.*

*57. A method according to claim 54 wherein the temperature sensed is the recipient's rectal temperature.*

*58. A method according to claim 54 wherein the temperature sensed is representative of the whole body temperature of the recipient.*

*59. A method according to claim 54 comprising the additional steps of selecting a target temperature below normothermia and maintaining the temperature of at least the tissue or organ at the target temperature after said target temperature has been reached.*

*60. A method according to claim 59 comprising the additional steps of adding heat when the sensed temperature is below the target temperature, and removing heat from the blood when the sensed temperature is above the target temperature.*

*61. A method according to claim 36 wherein Step a comprises inserting a heat exchange catheter having a heat exchange region into the vasculature of a recipient and positioning the catheter such that it exchanges heat with blood flowing to the organ or tissue to maintain the tem-*

*perature of the organ or tissue at about the temperature at which significant anti-platelet activity is effected.*

* * * * *